US00PP24714P3

(12) United States Plant Patent
Dibley

(10) Patent No.: US PP24,714 P3
(45) Date of Patent: Jul. 29, 2014

(54) ***STREPTOCARPUS* PLANT NAMED 'SLSPC16-0'**

(50) Latin Name: ***Streptocarpus* hybrid**
Varietal Denomination: SLSPC16-0

(71) Applicant: Lynne Dibley, Ruthin (GB)

(72) Inventor: Lynne Dibley, Ruthin (GB)

(73) Assignee: Dibley's Nursery (GB)

( * ) Notice: Subject to any disclaimer, the term of this patent is extended or adjusted under 35 U.S.C. 154(b) by 0 days.

(21) Appl. No.: 13/694,738

(22) Filed: Dec. 27, 2012

(65) Prior Publication Data

US 2014/0189918 P1 Jul. 3, 2014

(51) Int. Cl.
*A01H 5/00* (2006.01)

(52) U.S. Cl.
USPC ..... Plt./333

(58) Field of Classification Search
USPC ..... Plt./333
See application file for complete search history.

*Primary Examiner* — Anne Grunberg
(74) *Attorney, Agent, or Firm* — Cassandra Bright

(57) ABSTRACT

A new and distinct *Streptocarpus* cultivar named 'SLSPC16-0' is disclosed, characterized by unusual flower markings, red-purple upper lobes and yellow lower 3 lobes as well as multi-flowering. The new variety is a *Streptocarpus*, suitable as an outdoor garden or container plant.

2 Drawing Sheets

Figure 1:
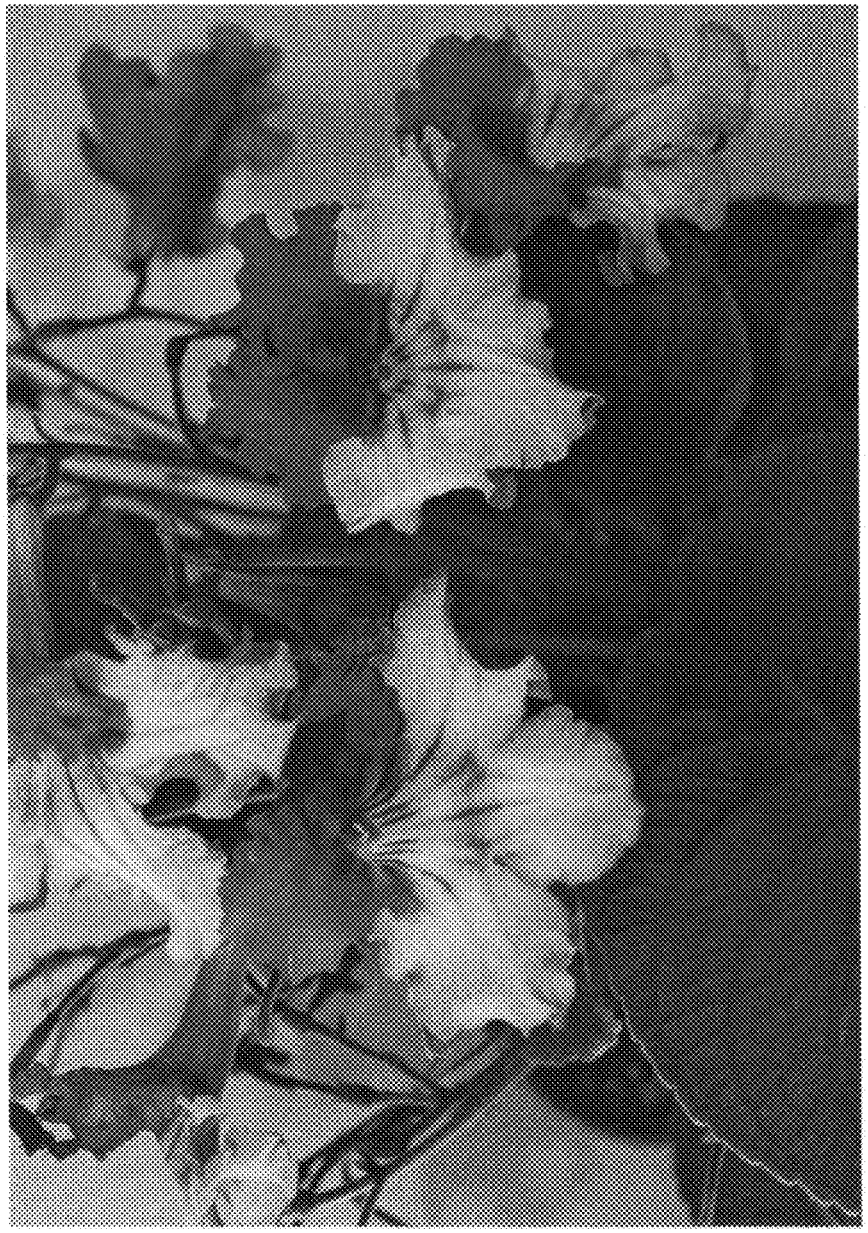

Latin name of the genus and species: *Streptocarpus* hybrid.
Variety denomination: 'SLSPC16-0'.

The new *Streptocarpus* cultivar is the product of a planned breeding program by the inventor Lynne Dibley, a citizen of United Kingdom. The breeding program was carried out at a commercial nursery in Ruthin, United Kingdom. The objective of the breeding program was to develop new *Streptocarpus* varieties for ornamental purposes.

The new variety resulted from the crossing of the seed parent, an unnamed, unpatented proprietary *Streptocarpus* seedling with the pollen parent, an unnamed, unpatented proprietary *Streptocarpus* seedling in 2010. The new variety was discovered in 2011 by the inventor in a group of seedlings resulting from the 2010 crossing, at a commercial nursery in Ruthin, United Kingdom.

Asexual reproduction of the new cultivar 'SLSPC16-0' by vegetative cuttings was first performed at a commercial greenhouse in Ruthin, United Kingdom in 2011. Subsequently at least three generations have been produced from vegetative cuttings, and have shown that the unique features of this cultivar are stable and reproduced true to type.

SUMMARY OF THE INVENTION

The cultivar 'SLSPC16-0' has not observed under all possible environmental conditions. The phenotype may vary somewhat with variations in environment such as temperature, day length and light intensity, without however, any variance in genotype.

The following traits have been repeatedly observed and are determined to be the unique characteristics of 'SLSPC16-0'. These characteristics in combination distinguish 'SLSPC16-0' as a new and distinct *Streptocarpus* cultivar:

1. Yellow coloration of lower lobes.
2. Highly floriferous plants.

3. Red-purple upper lobes.
4. Unusual flower markings.

COMPARISON TO THE PARENT VARIETIES

Plants of the new cultivar 'SLSPC16-0' are similar in most horticultural characteristics to plants of the unnamed, unpatented proprietary seed parent. However, the new variety has a larger overall flower and smaller leaf size than the seed parent. Additionally, plants of 'SLSPC16-0' produce flowers with different coloration and marking than flower of the seed parent, as well as shorter peduncles than the seed parent.

Plants of the new cultivar 'SLSPC16-0' are similar in most horticultural characteristics to plants of the unnamed, unpatented proprietary pollen parent. However, the new variety has a larger overall flower and smaller leaf size than the pollen parent. Additionally, plants of 'SLSPC16-0' produce flowers with different coloring and markings than the pollen parent.

COMPARISON TO COMMERCIAL VARIETY

The new cultivar can be compared to the commercial variety 'Harlequin Blue', unpatented. Plants of the two cultivars are similar in most horticultural characteristics, however, plants of 'SLSPC16-0' produce more leaves as well as flowering later than 'Harlequin Blue'. Additionally, plants of 'SLSPC16-0' produce larger flowers with different upper lobe coloring and longer peduncles than 'Harlequin Blue'.

The new cultivar can be compared to the commercial variety 'Bethan', unpatented. Plants of the two cultivars are similar in most horticultural characteristics, however, plants of 'SLSPC16-0' produces larger flowers with different flower markings, than found on flowers of 'Bethan'. Additionally, plants of 'SLSPC16-0' produce longer peduncles and are later flowering than 'Bethan'.

BRIEF DESCRIPTION OF THE PHOTOGRAPHS

The accompanying photograph in FIG. 1 illustrates in full color a typical flower of 'SLSPC16-0'.

Figure 2:
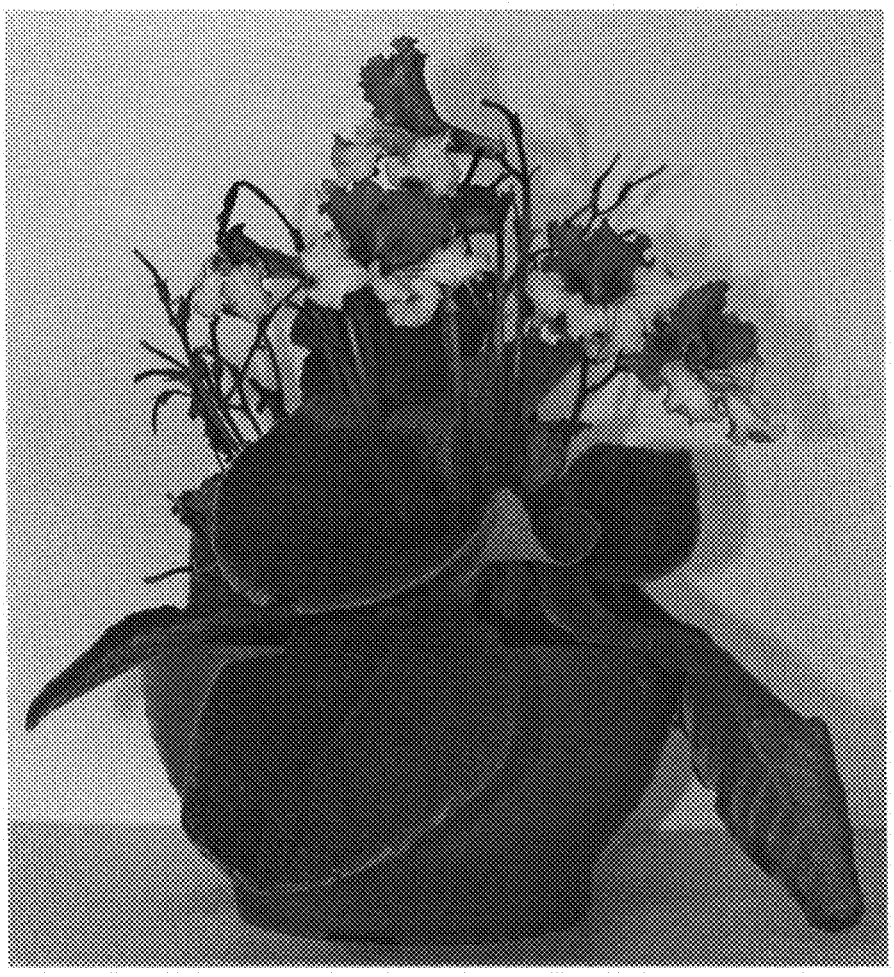

FIG. 2 illustrates a typical plant of 'SLSPC16-0' grown in a greenhouse, in a 1 gallon commercial pot. Age of the plant photographed is approximately 30 weeks from a rooted cutting.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001 except where general terms of ordinary dictionary significance are used. The following observations and measurement describe 'SLSPC16-0' plants grown in a commercial greenhouse in Oxnard, Calif. The growing temperature ranged from approximately 12° C. to 30° C. The greenhouse is subject to partial shade. General light conditions are bright, normal sunlight with some shade during the brightest part of the day. Measurements and numerical values represent averages of typical plant types.

Botanical classification: *Streptocarpus* hybrid 'SLSPC16-0'.

PROPAGATION

Time to initiate roots: About 20 to 25 days at approximately 21 to 25° C.

Root description: Fine, fibrous.

PLANT

Growth habit: Upright.

Age of the plant described: Approximately 30 weeks from a well rooted cutting.

Pot size of plant described: 6 inch pot.

Height: Approximately 15 cm from soil line to top of foliar plane. Approximately 21 cm to top of highest flower.

Plant spread: Approximately 31 cm at widest point.

Growth rate: Moderate.

Branching characteristics: Basal rosettes of foliate, no stem, no branches.

FOLIAGE

Leaf:

*Arrangement*.—Rosette.

*Quantity*.—Average 12 to 15 leaves.

*Average length*.—Approximately 15 cm.

*Average width*.—Approximately 11 cm.

*Shape of blade*.—Obovate.

*Apex*.—Acute.

*Base*.—Attenuate.

*Margin*.—Crenate.

*Appearance of top surface*.—Matte.

*Appearance of bottom surface*.—Matte.

*Pubescence*.—Very short, stiff, but not sharp, less than 1 mm hairs, densely covering top and bottom leaf surfaces.

*Aspect*.—Very slightly undulating, overall leaf, including petiole, reflexes downward. Leaf blade slightly folds up from the mid vein.

*Color*.—Young foliage upper side: Near RHS Green 137B. Young foliage under side: Near RHS Green 138C. Mature foliage upper side: Near RHS Green 137A. Mature foliage under side: Near RHS Yellow-Green 144D.

*Venation*.—Type: Pinnate. Venation color upper side: Near RHS Green 143C. Venation color under side: Near RHS Green 143C.

*Petiole*.—Length: Average range between 1.5 cm to 5.0 cm. Diameter: Approximately 1.0 cm. Color: Near RHS Yellow-Green 144B. Texture: Pubescent.

FLOWER

Natural flowering season: Continuous.

Inflorescence and flower type and habit: Racemes of trumpet-shaped flowers.

Approximate quantity of flowers per plant: Approximately 15 mature and immature flowers per plant.

Flowers: Persistent.

Inflorescence:

*Diameter of entire inflorescence*.—Approximately 10.0 cm.

*Depth of inflorescence*.—Approximately 8.0 cm.

Individual flower bud:

*Shape*.—Tubular.

*Length*.—Approximately 1.5 cm.

*Diameter*.—Approximately 0.4 cm.

*Color*.—Near RHS Yellow-Green 144A, heavily flushed Greyed-Purple N187A.

Flowers:

*Flower length*.—7.5 cm.

*Flower width*.—6.0 cm.

*Upper petals* (*upper lip*).—Number: 2, fused together at base. Length: 2.5 cm. Width: 2.5 cm. Shape: Obicular. Apex: Obtuse, ruffled. Margin: Entire. Texture: Velvety, all surfaces. Highly pubescent outersurface. Color: When opening: Inner surface: RHS Red-Purple 61A. Outer surface: RHS Red-Purple 61A. Fully opened: Inner surface: RHS Red-Purple N74A. Outer surface: RHS Red-Purple 72B. Aging: Inner surface: RHS Red-Purple N72A. Outer surface: RHS Red-Purple N74C.

*Lower petals* (*lower lip*).—Quantity: 3. Length: 2.5 cm. Width: 2.8 cm. Shape: Orbicular all 3 petals fused together at base. Apex shape: Obtuse, with minutely shallow lobes. Ruffled appearance. Color: When opening: Inner surface: RHS Yellow-Orange 18C. Outer surface: RHS Red-Purple N74D. Fully opened: Inner surface: RHS Yellow 10C. Outer surface: RHS Red-Purple N74D. Aging: Inner surface: RHS Yellow-Orange 18C, flushed Red-Purple 72B. Outer surface: RHS Purple 75A.

*Throat*.—Length: 3.5 cm. Width: 1 cm, at widest point. Texture: glabrous, shiny. Color: When opening: Inner surface: Striped, White N155C, Red-Purple 72A, Yellow 7A. Outer surface: RHS base White N155C, most of surface Red-Purple 72A. Fully opened: Inner surface: Striped, White N155C, Red-Purple 72A, Yellow 7A. Outer surface: RHS base White N155C, most of surface Red-Purple 72A. Aging: Inner surface: Striped, Mainly Red-Purple 77B, some stripes Yellow 9B and White N155C. Outer surface: RHS Purple 77C.

Sepals:

*Quantity*.—Average 5.

*Shape*.—Narrow deltate, base fused.

*Length*.—Approximately 0.7 cm.

*Width*.—Approximately 0.2 cm.

*Apex*.—Acute.

*Base*.—Fused.

*Margin*.—Entire.

*Texture*.—Highly pubescent, all surfaces.

*Color*.—Upper Surface: Near RHS Green 137A. Lower Surface: Near RHS Green 137A.

Peduncle:

*Length*.—Longest average 15 cm. Shortest average 8 cm.

*Diameter*.—Approximately 0.4 cm.

*Texture*.—Densely pubescent.

*Color*.—Near RHS Yellow-Green 144A.

*Orientation*.—Approximately 90 to 75 degree angle from rosette Moderate outward curvature on peduncles emerging farther from center.

Pedicel:

*Length*.—Average 1.8 cm.

*Diameter*.—Approximately 0.3 cm.

*Texture*.—Soft, dense pubescence.

*Color*.—Near RHS Green 138A.

*Orientation*.—Approximately 45 degree angle from peduncle. Straight, or outwardly curved.

Fragrance: Faint, slightly sweet.

REPRODUCTIVE ORGANS

Stamens:

*Number*.—2.

*Filament length*.—Approximately 0.5 cm, unfused section.

Anthers:

*Length*.—Approximately 0.2 cm.

*Shape*.—Bi-lobed.

*Color*.—Near RHS Greyed-Yellow 160D.

*Pollen*.—Not observed.

Pistil:

*Number*.—1.

*Length*.—Approximately 2.2 cm.

*Style*.—Length: Approximately 2.0 cm. Color: Near RHS Greyed-Purple N187B.

*Stigma*.—Shape: Bifurcate. Color: Near RHS Greyed-Purple N187C.

OTHER CHARACTERISTICS

Seeds and fruits: Not observed.

Disease/pest resistance: Neither resistant nor susceptible to normal diseases and pests of *Streptocarpus*.

Temperature tolerance: USDA zones 9-11.

What is claimed is:

1. A new and distinct cultivar of *Streptocarpus* plant named 'SLSPC16-0' as herein illustrated and described.

* * * * *